United States Patent [19]

Ryan et al.

[11] 4,326,528
[45] Apr. 27, 1982

[54] ELASTIC LEGGED DIAPERS

[75] Inventors: Lenore S. Ryan; Frank C. Murray, both of Appleton; Ann M. Sprangers, Neenah; William J. Santoski, Appleton; Michael A. Sciaraffa, Greenville; Kent W. Abel, Black Creek; Harold F. Donnelly, Menasha, all of Wis.

[73] Assignee: Kimberly-Clark Corporation, Neenah, Wis.

[21] Appl. No.: 138,255

[22] Filed: Apr. 7, 1980

[51] Int. Cl.³ .............................................. A61F 13/16
[52] U.S. Cl. ................................... 128/287; 128/284; 128/290 R
[58] Field of Search .................... 128/290 R, 284, 287, 128/29 R

[56] References Cited
U.S. PATENT DOCUMENTS
3,860,003 1/1975 Buell .................................. 128/287

FOREIGN PATENT DOCUMENTS
2016262 9/1979 United Kingdom ................. 128/287

Primary Examiner—Marion Mc Camish
Assistant Examiner—Beverly Johnson
Attorney, Agent, or Firm—Howard Olevsky; William D. Herrick

[57] ABSTRACT

An elastic leg disposable diaper is provided which, when worn, forms an absorbent pocket with planar sides in the crotch area. The pocket has flex regions in the crotch area of the diaper which define a bottom crotch profile and elastic edges which encircle the leg of the baby and semirigid absorbent-containing planar sides extending upward from the flex regions to the elastic edges. The diaper at its lowest profile in the crotch area is either planer or upwardly arcuate when the baby is standing. The stiffness of the sides is generally correlative of a Taber stiffness value of at least seven gm-cms for the absorbent material located thereon.

25 Claims, 16 Drawing Figures

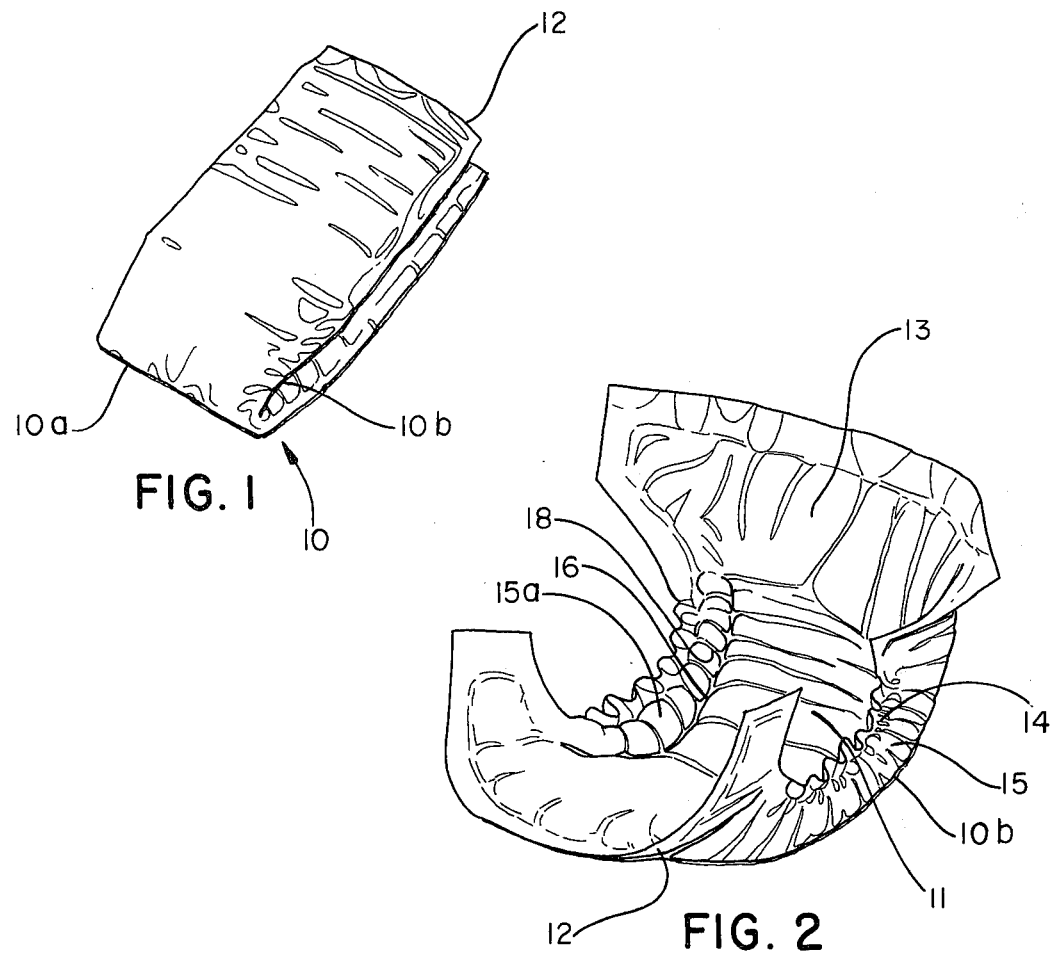
FIG. 1
FIG. 2
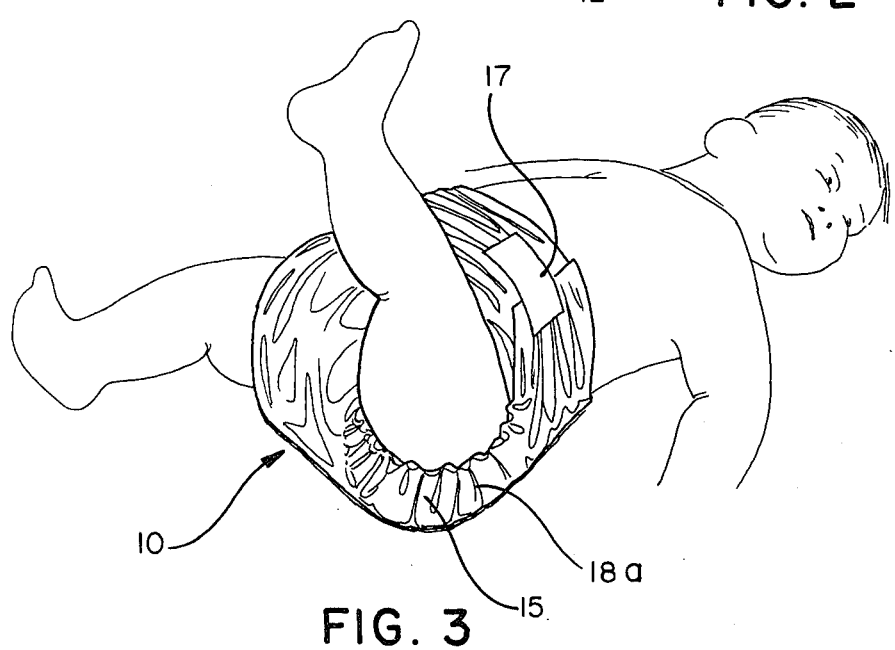
FIG. 3

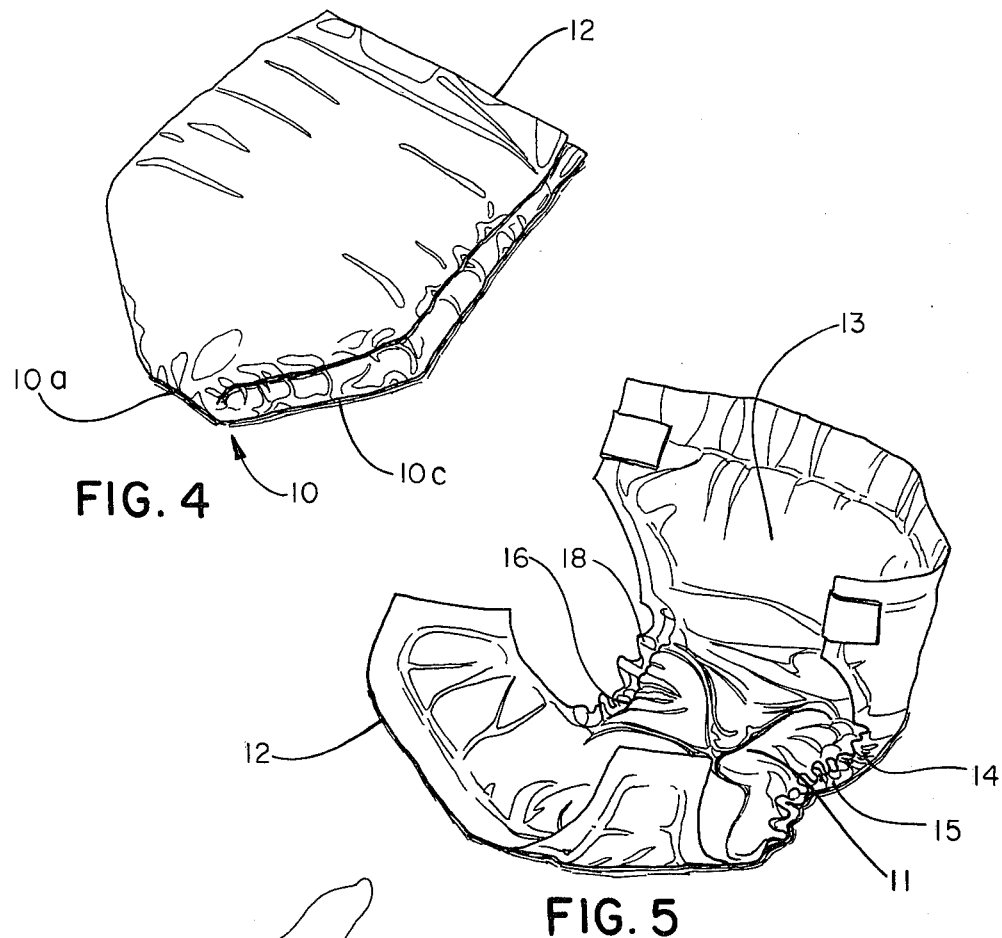
FIG. 4
FIG. 5
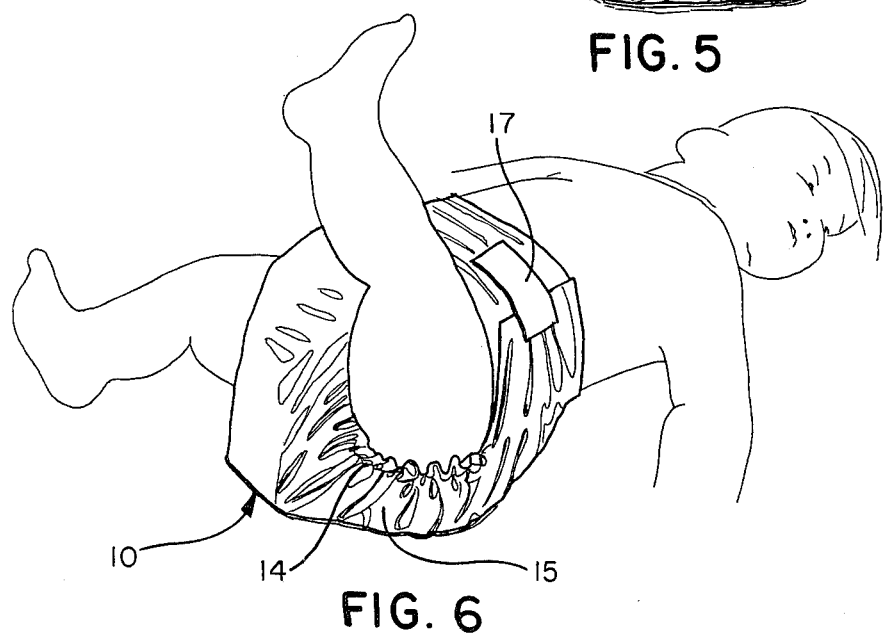
FIG. 6

ELASTIC LEGGED DIAPERS

FIELD OF THE INVENTION

The subject invention relates to an elastic legged disposable diaper and particularly a diaper having waste retentive sides.

BACKGROUND OF THE INVENTION

In the past decade, disposable diapers have become increasingly popular. One of the recent developments in this area is the inclusion of elasticized leg openings in the diaper construction. The result of the utilization of elastic legged diapers has been to provide a diaper having a better appearing fit and better fit in some instances.

Such an elastic legged diaper is described in U.S. Pat. No. 3,860,003 (issued to Kenneth Barclay Buell). The integral disposable diaper described therein has the traditional components, a fluid-permeable facing sheet, a fluid-impervious backing sheet and an absorbent material sandwiched between the sheets and adhesively bonded to the backing sheet. The patent further discloses a side flap in the crotch area with the elastic means secured to the side flap in an elastically contractible condition to gather the side flap. The distance between the elastic edge and the absorbent material in the crotch area is at least ¾" and it is indicated that absorbent material may be present in the side portion. As set forth therein, if fluff absorbent is included in the side flap it is designed to be extremely flexible, i.e. having a maximum Taber stiffness of six gm-cms and preferably less than three and most preferably less than 0.5. (Taber stiffness as used throughout this application refers to gm-cm units of measurement.)

An example of another disposable diaper with elastic legged portions is that disclosed in U.S. Pat. No. 4,050,462 (issued to Lin-Sun Woon and Dan D. Endres). This patent teaches the concept of providing increasing amounts of absorptive material in the crotch area by utilizing the elastic in relatively close proximity to the edge of the absorptive component with the elastic being attached to either the facing or backing sheet. In this patent, by placing the elastic within ½" of the absorbent material, gross transverse rugosities are formed which provide this extra absorbent amount of material in the crotch area. In both of these patents, extended elastic material is attached to the crotch area and, when the elastic is relaxed the elasticized leg area is formed.

While elastic legged diapers such as those represented by the above described patents have been gaining in popularity, recently, the performance of the diapers from the standpoint of waste containment in the leg areas has not been as good as might be expected. Some leakage at the leg is still possible and has been most often noticed on active children.

It has now been found that the placement of the elastic relative to the edge of the fluff and the presence or absence of side flaps are not the only features to be considered for maximum use of absorbent material and retention of waste products. It is the particular configuration of the diaper profile as interrelated to these features which enables the maximum degree of waste retention and comfort to be obtained in elastic legged disposable diapers.

SUMMARY OF THE INVENTION

According to this invention a unitary elasticized disposable diaper having a fluid-pervious facing sheet, a fluid-impervious backing sheet and an absorbent material disposed between the facing and backing sheets, a waist section and an elasticized crotch section is provided. The elasticized crotch section is characterized by a planar or upwardly arcuate portion at the lowest profile of the diaper when worn by the baby when standing. In addition, the diaper has a flex region defining the edge of the planar or upwardly arcuate portion at either side of the lower crotch profile and a planar relatively rigid absorbent-containing side portion extending from each flex region to the elastic edge of the diaper as it encircles the upper portion of the baby's legs. This planar absorbent-containing stiff side, in conjunction with the flat or upwardly arcuate bottom profile in the crotch portion define an absorbent containment pocket in the area most susceptible to side leakage.

For purposes of this invention, a diaper having a stiff lower profile crotch section is highly desirable and it is absolutely essential that the side formed between the flex region and the elastic also be stiff. It may, in fact, be desirable in some instances to have the stiffness at the side portion greater than that in the bottom profile of the diaper. Stiffness in the side and along the bottom is needed to help preserve the configuration of the diaper.

As used througout this specification, the planar or upwardly acruate bottom profile in the crotch section refers to the profile at the lowest possible portion of the diaper apparent when the baby is standing. Of course, when the baby does sit the profile in that area becomes distorted although resistance to distortion is highly desirable because of the importance of the overall configurational aspects of this invention and the interrelationship of each of these parameters to each other to the effectiveness of the diaper in its entirety. For purposes of this invention, a Taber stiffness of 7 is a realistic minimum for the bottom portion of the diaper.

Rigidity, not only in the lower profile which is necessary but, contrary to Buell, in the sides as well, can be obtained by the utilization of a stiff facing, stiff backing or stiff absorbent batt or combinations of the three. The desired rigidity of the pocket side can be formed in much the same manner.

In addition, adhesive lines can be added to the backing in the area of the planar side to add rigidity and aid in positioning the absorbent material and maintaining its position when the diaper is worn. A Taber stiffness of at least 7 and preferably greater than 8 in the planar side of the pocket with conventional flexible facing or backing material is representative of the type of stiffness which is minimal to the preservation of the planar configuration. This stiffness level is a minimum and presupposes no added rigidity from either the facing or the backing. Obviously, either can contribute substantially of this stiffness value.

It has been found that a nearly uniform Taber stiffness between sides and bottom is preferred from a manufacturing standpoint but ranges of 1:4 to 4:1 may be utilized in particular cases with ranges of 1:2 to 2:1 being particularly preferred. Stiffer sides can be obtained by the addition of adhesive lines and increases stiffness in either portion relative to the other can be developed by utilizing inserts of more rigid absorbent materials instead of or in addition to conventional diaper fluff.

One of the characteristics of this invention is that rugosities which may be similar in type to those described in the Woon-Endres patent are formed in the planar side of the pocket. The extent of the rugosities formed primarily depend on the stiffness of the absorbent and the elastic tension of the elastic. These rugosities start in the area of the elastic and appear as radial "spokes" extending outward from the elastic areas to the flex region. Once these "spokes" descend past the gathering area adjacent the elastic a distance of ¼–1 inch they are essentially uniform in character until they reach the flex region.

The presence of the rugosities provides extra absorbent material as well as containment channels at the sides of the diaper. In contrast with the Woon-Endres patent, however, the flex region provides a clear line of demarcation for the rugosities, i.e. they abruptly cease at the flex region.

While central rugosities of a greatly reduced height and width may be formed between the flex regions, these originate anew at the flex regions and are discontinuous with the side rugosities described above.

As mentioned above, rugosities are produced by elastic acting on the flexible absorbent material. The absorbent, which is conventionally fluff, therefore, cannot be overly rigid if the rugosities are to be formed. The maximum amount of rigidity is determined by the range of elastic tension range which can be utilized from the standpoint of fit, containment and comfort. It has been found that elastic tension of between 50 and 600 grams force when measured at 100% elongation by ANSI/ASTM D 412-75 provides an acceptable range for the purposes of this invention. Intermediate values of about 90–200 grams force are especially preferred.

While Taber stiffness values of at least 7 for the absorbent are necessary for configurational integrity, the upper limit is determined by the ability of the elastic to gather the fluff at the upper area of the side of the pocket to form the elasticized sealed edge around the legs of the baby. If the fluff is too stiff to be gathered, the elastic will not readily conform to the leg contours. As a result, Taber stiffness values of 75 form a realistic upper stiffness limit.

The pocket of this invention can also be characterized in other terms. For example, the distribution of absorbent between the sides and the bottom portion is important both from maximum absorbent utilization and conformability. It has been found that a weight ratio of 1:25 to 2:1 of absorbent of one planar side to bottom provides a satisfactory distribution which takes into account the variety of pocket configurations possible with the teachings of this invention bearing in mind the necessarily limited dimensions of the bottom and sides. It has been found, further, that ratios of 1:5 to 1:1 are particularly preferred. The preferred ratios providing sufficient absorbent in the sides to significantly aid in fluid retention.

The configuration of the pockets of this invention can also be defined by a ratio of the comparison of the area of one of the sides to the bottom. This ratio is between about 1:12 and 12:1 with particularly advantageous fit parameters occurring when the ratio is between about 1:2 and 2:1.

BRIEF DESCRIPTION OF DRAWINGS

There are several variants in overall configuration possible to produce a diaper embodying the features of this invention. Examples of these embodiments can be seen from the drawings in which:

FIGS. 1, 4 and 7 are perspective views of different embodiments of the folded diaper of this invention.

FIGS. 2, 5 and 8 are perspective views of the diaper as it would appear in an opened configuration.

FIGS. 3, 6 and 9 are perspective views of the diapers of FIGS. 1 and 2, 3 and 4, and 5 and 6 as they appear when worn by the baby.

Figure 11:
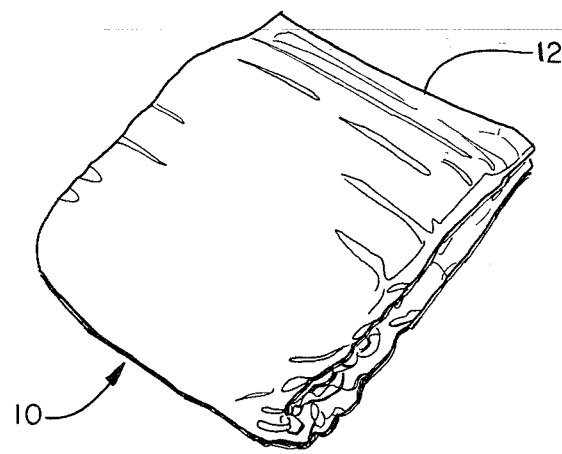
FIGS. 11, 12 and 13 show the prior art diaper described in the Woon-Endres patent in its folded and opened configuration and also as it is used.
Figure 12:
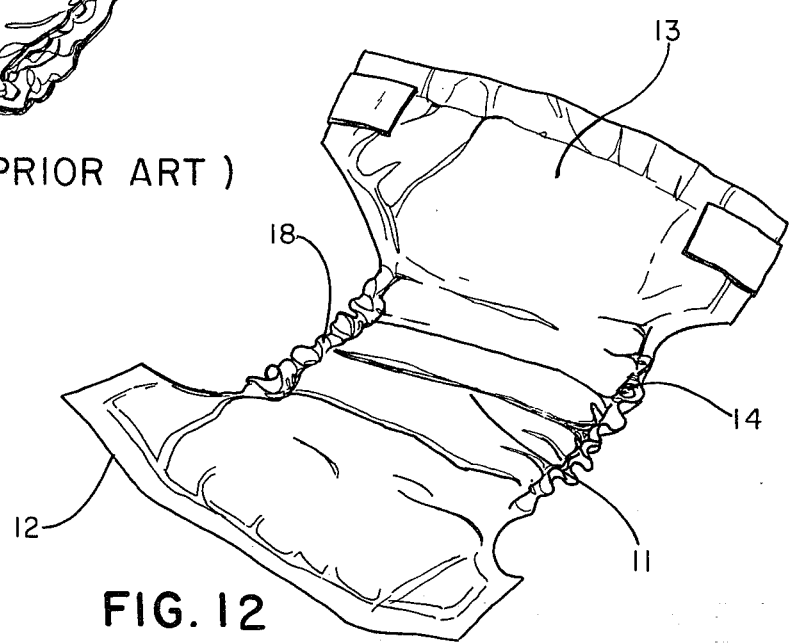

As can be seen from FIGS. 1, 2 and 3, a rectangular fold diaper which in its folded form tends to lie flat but, when opened, has an overall C-shaped configuration. The absorbent pocket as can be seen from FIGS. 2 and 3 provides not only for absorbency and containment but, due to the space between the pocket and the baby's crotch provides for circulation of air. In addition, there is substantial freedom from chafing and space for stools and what appears to be a more comfortable fit about the crotch region. As can be seen from FIG. 1, the diaper is composed of a waist section 12, a crotch section 10, a fold line 10A at the outward portion of the diaper and an inward fold line 10B. As can be seen from FIG. 2, the diaper in its open configuration has a pocket formed as illustrated on the outer surface of the diaper backing 13 and at the inner surface of the facing portion 13A. The gathered elastic shown in its relaxed contracted state at 14 defines the leg opening. Rugosities are formed in the crotch area 11 by the elastic at the edge of the fluff. Due to the flex region 16 which extends to form the bottom of the pocket, the rugosities are not as intense and defined as those present in the prior art as can be seen in FIG. 11. As can be seen from FIGS. 2 and 3 the pocket formed from the flex region 16 and the planar side portions 15–15A as well as the elastic 14 bows slightly outward when the diaper is in its open configuration and also slightly outward as it appears about the baby. The side rugosities are shown generally at 18 in FIG. 2 which depicts the ridges which are relatively deep compared to those extending between the fold regions. The spokes 18A, as can be seen from FIG. 3 radiate outward from the elastic as it is attached and correspond to the rugosities 18 on its inner side of the diaper.

FIGS. 4, 5, and 6 represent a second embodiment of this invention with the same numbers used to identify identical features. As can be seen from FIG. 4, the particular folded configuration of this diaper is substantially different while rugosities 11 are present, as can be seen in FIG. 5, they are substantially less pronounced. The pocket formed by this tuck fold, i.e. the inwardly tapering extended fold in the crotch area produces a pocket which is very deep in its side configuration but narrow at the lowest profile portion of the crotch area. This embodiment is also illustrative of the relatively intense side rugosities in the area intermediate the flex regions.

Figure 7:
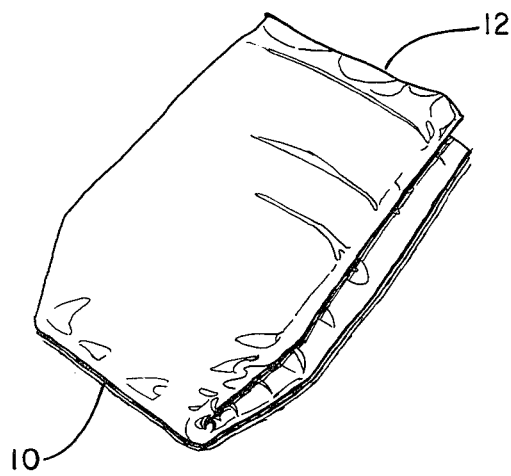
Figure 8:
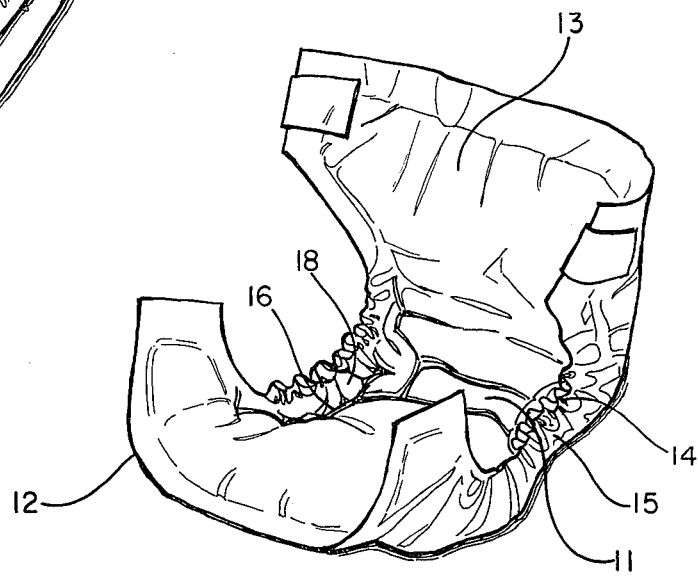
Figure 9:
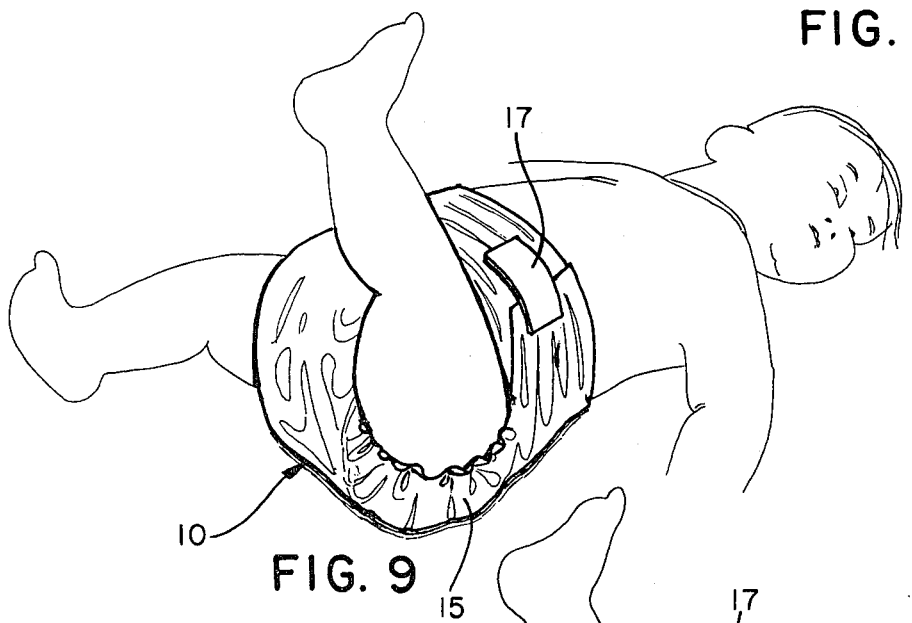
Figure 10:
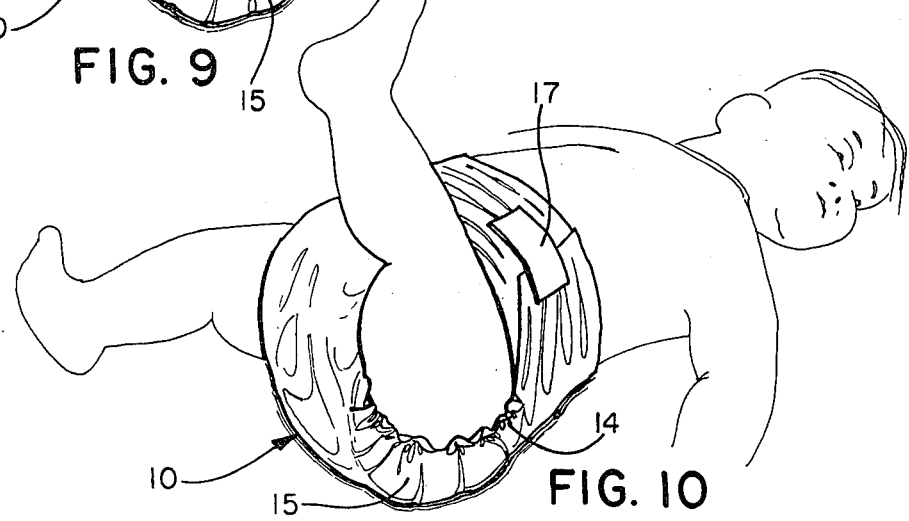
FIG. 10 is a perspective view of a diaper similar to FIG. 9.

A third embodiment can be seen at FIGS. 7, 8 and 9. This is an embodiment which is intermediate in configurational extremes between the embodiments depicted in the earlier figures. The only difference between FIGS. 9 and 10 is the upwardly arcuate bottom profile and FIG. 10 is representative of that profile on the baby. The bottom profile 10, at FIG. 10, in contrast to that of the earlier Figures is shown here drawn upwardly arcuate. This particular configuration is likely to result where the facing and backing liners are used to give structural rigidity to the diaper.

Figure 13:
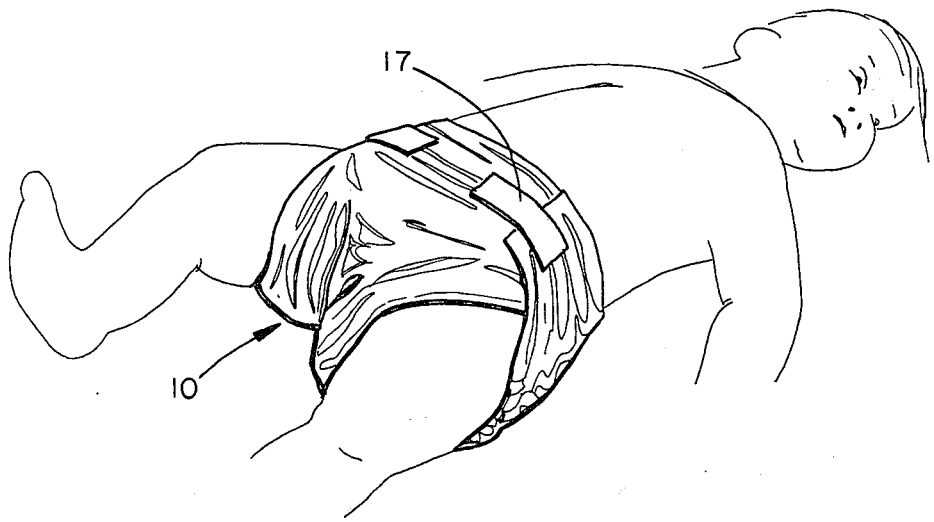

A graphic comparison between the effect of the configuration of the prior art and the configuration of the subject matter of this invention can be seen by comparing FIG. 13 with FIGS. 3, 6 and 10. As can be seen from the bottom profile 10, at FIG. 13, a continuous extension in the crotch area provides for a crushing of the absorbent material and an inverted V-shaped crotch configuration. The upward point of the V provides the top of dual outwardly extending troughs which define pathways for liquid and solid waste migration towards and eventually out of the elasticized leg openings of the diaper. By providing the diaper configuration of this invention in which the bottom portion of the diaper is planar and upwardly arcuate and, compared to the prior art, somewhat reduced in length and a configuration which provides the pockets described previously, the V-shaped exit trough described above is less likely to occur and, even if after extended use it does occur, the containment pockets tend to mitigate its effect.

With regard to the side of the pocket, it is necessary to retain the planar configuration as long as possible when the diaper is in use. In other words, even if the baby is sitting, walking or doing any of the other customary motive operations it is highly desirable that the planar side configuration be maintained.

Figures 14A, 14B, 14C:
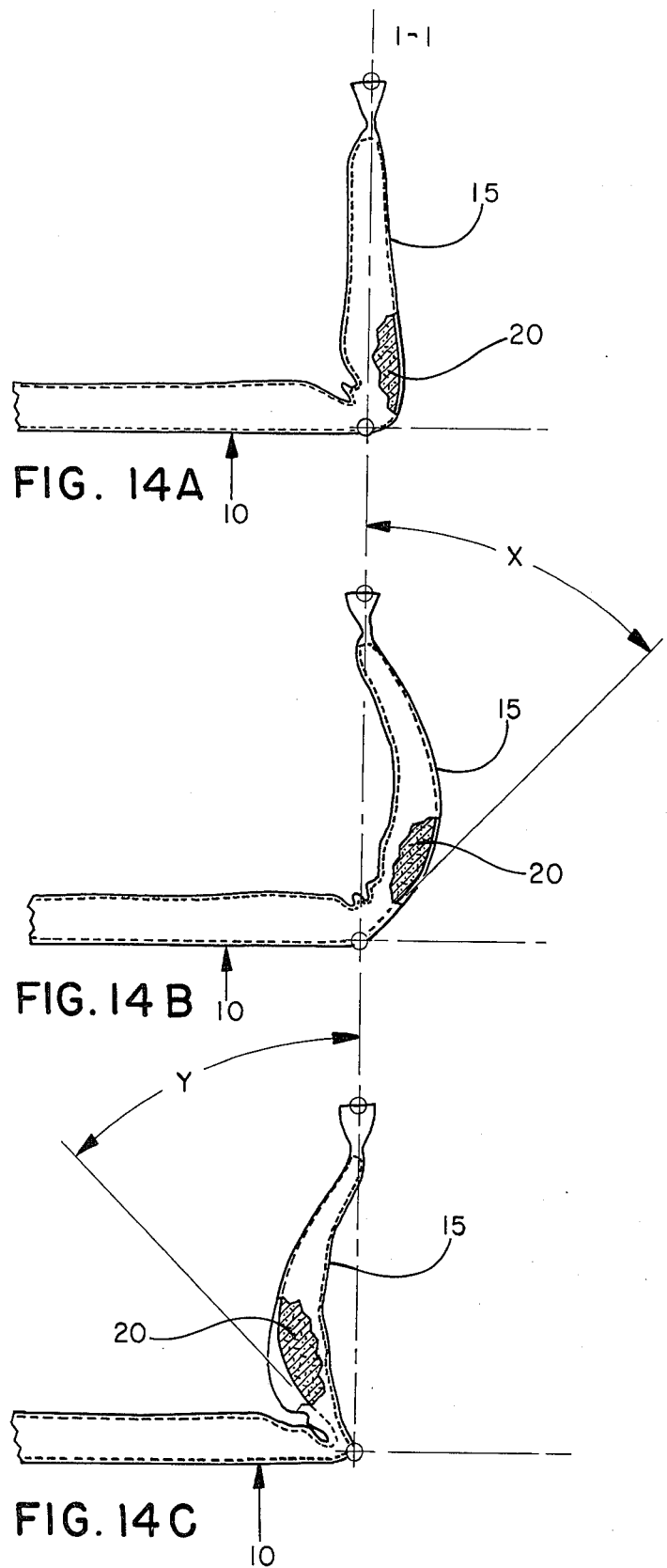
FIGS. 14A, B and C are a front cross-sectional of the side and the pocket of the diaper of this invention. With regard to the Figures, in all instances, like numbers refer to like components.

While this planar configuration may be slightly inwardly or outwardly arcuate, for purposes of this invention, planar variations of greater than 15° are undesirable as measured from a plane most nearly approximating that of the diaper. Curvatures of greater than 45° have generally been found to be undesirable because of the likelihood of compression of the pocket-side with the effective destruction of the pocket configuration. The plane used for measuring the planar configuration is that which extends through the elasticized edge and the flex region, and planar in the context of this application refers only to that plane. The planar variations described refer to the angle formed by a line tangential to the curvature of the fluff in the side at the flex region and the plane described above. As can be seen from FIG. 14C, the diaper backing 15 even though it is adhesively attached to the absorbent areas 20 may pillow slightly adjacent the attachment. The measurement is therefore best determined from the absorbent edge. Angles X and Y in FIGS. 14B and 14C are both 45° although they are determined outwardly and inwardly respectively of the plane represented by dashed lines 1—1. FIG. 14A represents the currently preferred embodiment where there is virtually no space between the absorbent material because of the presence of extra rigidifying glue lines.

DESCRIPTION OF THE PREFERRED EMBODIMENTS

While configurations may vary, it is generally preferred that the planar or upwardly arcuate portion defined by the distance between the flex region be between about 1.5 in. and 5.0 in. with the length of the planar side of the pocket as measured linearly between the flex region and the elastic is not greater than about 7 in. with this value dependent upon configuration. This 7 in. value is generally found with the tuck fold configuration and when this particular configuration is utilized in the smaller sizes, the planar side may not "open" all the way. When this happens, the planar side will have a single inward V. This is a modification of the definition of planar within the scope of this invention. These extremes in configuration take into account smallest desirable crotch width for an infant and largest crotch width for a toddler ranging in weight up to about 40 pounds. Generally ranges in crotch width for each of these standard sizes are infant 6.0 in. to 10 in., medium 7.0 in. to 12.0 in., and toddler 8.0 in. to 14 in. The smaller numbers in these ranges refer to the contoured diapers and the larger numbers to the noncontoured diapers. The planar sides of the pocket will, of course, vary with the particular configuration chosen for folding and can be as little as ½ in. although minimum pocket distances of at least 1.0 in. are desirable and 1.5 in. to 2.5 in. are preferred. It is generally not desirable from the standpoint of overall diaper fit to have the bottom profile extending too far below the crotch area. This is particularly the case when additional layers of clothing are applied over the diaper. The distance of the pocket extension is therefore determined especially in larger sizes by this factor and the maximum value is therefore set by means other than pocket features or absorbency.

The minimum and maximum values given above are determined from the point on the flex region which is closest to the elastic line for both minimum and maximum values.

With regard to the flex region itself, it may be slanted inwardly or outwardly from the narrowest portion and may extend to the edge of the crotch area as shown in FIGS. 2, 5 and 9 or they may extend along the entire length of the diaper. In each of the Figures illustrated previously, it is apparent from the open configuration that these diapers are configured with a leg cutout, i.e. the inward curve at the crotch area shown in the open position is reduced in width from the waist area. Diapers which can essentially rectangular in configuration are also contemplated within the scope of this invention and a longitudinal fold region extending the length of such a diaper is a variant which is particularly adaptable to the rectangular configuration on the basis of easy folding and handling.

It is also contemplated that the flex region provide some aesthetic configuration for the diaper as a whole and may be arcuate or sinusoidal for example and, from the standpoint of pocket design, a variety of shapes are possible although difficulties in folding may inhibit the ultimate selection.

With regard to the flex region itself, "flex region" in this context refers to the area across the width of the diaper in the crotch, which defines the start of an upward directional change. This area is no greater than an inch width and may in fact be nothing more than a line. It may also be irregular in width and be linearly discontinuous. The predetermined nature can be established by folding, compressing, embossing or providing a seam in which the absorbent is not present. The particular means for obtaining the flex region as well as its configuration is immaterial as long as the flex region is, in itself, present.

Generally, diapers made according to this invention have a length not exceeding about 15 in. and a width in the waist area of 11 in. for the infant size and length and width dimensions between 16 in. and 20 in. and 12 in. and 15 in. for the medium and toddler size with intermediate dimensions for the medium diapers. Of course, according to the concept of this invention, these values are important as they interrelate particularly with the width of the diaper in the crotch area between the flex regions and the particular pocket configurations.

It is currently preferred that diapers made according to this invention utilize a conventional waist fastening means such as tape tabs in the waist portion for attachment although any fastening means commonly used for diapers can, in fact, be utilized for the diapers of the present invention.

What is claimed is:

1. In a unitary elasticized disposable diaper having a fluid pervious facing, a fluid impevious backing essentially coterminous therewith and an absorbent material positioned between said facing and said backing, a waist portion at each end of said diaper for securement about the waist of the baby when the diaper is worn, and an elasticized crotch portion the end waist portions having elastic attached near the periphery of each diaper side in the crotch portion and a flex region positioned inward from said elastic, absorbent being present between said elastic and said region, the improvement comprising providing the diaper with sufficient rigidity so that the lowest profile at the crotch area of the baby when the baby is standing is planar or upwardly arcuate in the area in the crotch between the predetermined directional change formed by the flex regions and the area between the flex regions and the elastic is planar and tends to remain planar even when the baby is sitting thereby forming a containment pocket.

2. The diaper according to claim 1 wherein the sides of the containment pocket have a Taber stiffness not less than 7.

3. The diaper according to claim 1 wherein the diaper pocket has a Taber stiffness of at least 7.

4. The diaper according to claim 1 wherein the configuraion between the flex regions is maintained at least partly by a relatively rigid backing.

5. The diaper according to claim 1 wherein the configuration between the flex regions is maintained at least partly by a relatively rigid liner.

6. The diaper according to claim 1 wherein the upwardly arcuate configuration is obtained and maintained by using heat shrinkable biaxially oriented backing.

7. The diaper according to claim 1 wherein the flex regions are formed by compression.

8. The diaper according to claim 1 wherein the flex regions are formed by embossing.

9. The diaper according to claim 1 wherein the flex regions are devoid of absorbent.

10. The diaper according to claim 1 wherein the distance between the flex regions and the elastic at its widest point is not greater than 7.0 inches.

11. The diaper according to claim 1 wherein the diaper assumes a tuck fold configuration when folded.

12. The diaper according to claim 1 wherein the diaper assumes a rectangular fold when folded.

13. The diaper according to claim 1 wherein the diaper assumes a rectangular-tuck fold when folded.

14. The diaper according to claims 1, 2, 3, 4, 5, 6, 7, 8, 9, 10, 11, 12 or 13 wherein rugosities are formed in between the flex regions and the elastic.

15. The diaper according to claim 1 wherein the flex regions are linear and essentially parallel to the elastic in the crotch area.

16. The diaper according to claim 1 wherein the flex regions are nonlinear.

17. The diaper according to claims 1, 2, 3, 4, 5, 6, 7, 8, 9, 10, 11, 12, 13, 15 or 16 wherein the ratio of absorbent weight in one of the sides to the bottom between the sides is from 1:25 to 2:1.

18. The diaper according to claims 1, 2, 3, 4, 5, 6, 7, 8, 9, 10, 11, 12, 13, 15 or 16 wherein the ratio of absorbent weight of one of the sides to the bottom between the sides is from 1:5 to 1:1.

19. The diaper according to claim 1 wherein the length is between 14.0 and 19.0 inches and the width in the waist edge is from 10 to 14 inches when the diaper is laid flat.

20. The diaper according to claim 1 wherein fastening means are included in the waist.

21. The diaper according to claim 20 wherein the fastening means are tape tabs.

22. The diaper according to claim 1 wherein elastic is present in the waist area.

23. The diaper according to claims 1, 2, 3, 4, 5, 6, 7, 8, 9, 10, 11, 12, 13, 15 or 16 wherein the elastic in the leg area has a tension value of between about 50 and 600 gms. force at 100% elongation.

24. The diaper according to claims 1, 2, 3, 4, 5, 6, 7, 8, 9, 10, 11, 12, 13, 15, or 16 in which the area ratio of one of the sides to the bottom is from 1:12 to 2:1.

25. The diaper according to claims 1, 2, 3, 4, 5, 6, 7, 8, 9, 10, 11, 12, 13, 15 or 16 in which the area ratio of one of the sides to the bottom is 1:2 to 2:1.

* * * * *